(12) United States Patent
Yazaki

(10) Patent No.: US 8,848,860 B2
(45) Date of Patent: Sep. 30, 2014

(54) X-RAY CT APPARATUS

(75) Inventor: Yujiro Yazaki, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 386 days.

(21) Appl. No.: 13/331,646

(22) Filed: Dec. 20, 2011

(65) Prior Publication Data

US 2012/0155605 A1 Jun. 21, 2012

(30) Foreign Application Priority Data

Dec. 20, 2010 (JP) .................................. 2010-282713

(51) Int. Cl.
 *A61B 6/03* (2006.01)
 *A61B 6/00* (2006.01)
 *H05G 1/34* (2006.01)

(52) U.S. Cl.
 CPC *H05G 1/34* (2013.01); *A61B 6/469* (2013.01); *A61B 6/488* (2013.01); *A61B 6/032* (2013.01); *A61B 6/405* (2013.01); *A16B 6/542* (2013.01)
 USPC .............................................. 378/8; 378/16

(58) Field of Classification Search
 CPC ........ A61B 6/032; A61B 6/405; A61B 6/469; A61B 6/488; A61B 6/542; H05G 1/34
 USPC ....................................... 378/16, 8, 108–110
 See application file for complete search history.

(56) References Cited

U.S. PATENT DOCUMENTS

| | | | |
|---|---|---|---|
| 5,379,333 A * | 1/1995 | Toth | 378/16 |
| 6,466,639 B2 | 10/2002 | Nukui et al. | |
| 6,507,639 B1 * | 1/2003 | Popescu | 378/108 |
| 6,862,336 B2 | 3/2005 | Nishide et al. | |
| 7,809,102 B2 | 10/2010 | Brada et al. | |
| 7,848,480 B2 | 12/2010 | Nakanishi et al. | |

FOREIGN PATENT DOCUMENTS

| | | |
|---|---|---|
| JP | 2004113791 | 4/2004 |
| JP | 2004321587 | 11/2004 |
| JP | 2007026965 | 2/2007 |
| JP | 2007185358 | 7/2007 |
| JP | 2010269048 | 12/2012 |

* cited by examiner

*Primary Examiner* — Allen C. Ho
*Assistant Examiner* — Danielle Fox
(74) *Attorney, Agent, or Firm* — Armstrong Teasdale LLP

(57) ABSTRACT

An X-ray CT apparatus is provided. The X-ray CT apparatus includes an X-ray tube configured to apply an X-ray onto a subject, a scan device configured to rotate the X-ray tube about the subject to perform an X-ray CT scan, a first control device configured to switch an X-ray output of the X-ray tube from a first level to a second level smaller than the first level when the X-ray tube is placed at a first view angle, and configured to switch the X-ray output from the second level to the first level when the X-ray tube is placed at a second view angle, and a second control device configured to set the first view angle and the second view angle such that an X-ray exposure dose reduced by setting the X-ray output of the X-ray tube smaller than the first level becomes even on right and left sides.

20 Claims, 15 Drawing Sheets

FIG. 6

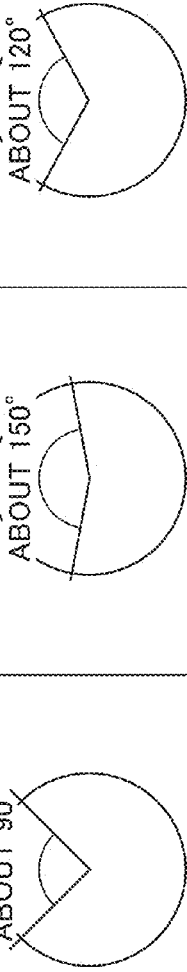

| IMAGING REGION | HEAD REGION /NECK REGION | | | CHEST REGION | | | ABDOMINAL REGION/OTHERS | | |
|---|---|---|---|---|---|---|---|---|---|
| REGION TARGET FOR EXPOSURE REDUCTION | CRYSTAL LENS/THYROID | | | MAMMARY GLAND | | | GENERATIVE ORGAN | | |
| MAJOR VIEW ANGLE RANGE FOR EXPOSURE REDUCTION | ABOUT 90° | | | ABOUT 150° | | | ABOUT 120° | | |
| TUBE CURRENT REDUCTION RATE k | 60% | | | 40% | | | 50% | | |
| | | FIRST SWITCH VIEW ANGLE θ1 | SECOND SWITCH VIEW ANGLE θ2 | | FIRST SWITCH VIEW ANGLE θ1 | SECOND SWITCH VIEW ANGLE θ2 | | FIRST SWITCH VIEW ANGLE θ1 | SECOND SWITCH VIEW ANGLE θ2 |
| GANTRY ROTATION TIME T [SECOND/ ROTATION] | 0.4 | −70° | +35° | | −110° | +65° | | −95° | +50° |
| | 0.6 | −65° | +40° | | −105° | +70° | | −90° | +55° |
| | 0.8 | −60° | +45° | | −100° | +75° | | −85° | +60° |
| | 1.0 | −60° | +45° | | −100° | +75° | | −85° | +60° |

X-RAY CT APPARATUS

CROSS REFERENCE TO RELATED APPLICATIONS

This application claims the benefit of Japanese Patent Application No. 2010-282713 filed Dec. 20, 2010, which is hereby incorporated by reference in its entirety.

BACKGROUND OF THE INVENTION

The present invention relates to an X-ray CT (Computed Tomography) apparatus, and more specifically to an X-ray CT apparatus which changes an X-ray output of an X-ray tube according to view angles.

There has been known, upon imaging using an X-ray CT apparatus, a method in which only when an X-ray tube is in a prescribed view angle range close to a tissue high in radiation sensitivity, an X-ray output of the X-ray tube is set smaller than a normal level to perform a scan (refer to, for example, Japanese Patent Publication Laid-Open No. 2004-321587 and abstract thereof). According to this method, it is possible to reduce the amount of radiation exposure to the tissue high in radiation sensitivity.

Tissues high in radiation sensitivity include crystalline lenses, thyroid, lacteal or mammary glands, a generative organ, etc. These tissues high in radiation sensitivity and their peripheral tissues are configured approximately in a laterally symmetrical manner as viewed from a subject. For this reason, in general, when the above method is used, a view angle range of an X-ray tube in which the level of an X-ray output is made smaller, is also attempted to be arranged in a laterally symmetrical manner on the basis of a view angle of the X-ray tube corresponding to the direction of the front of a subject, e.g., a view angle at which the X-ray tube is located directly above the subject.

The X-ray output of the X-ray tube has, however, a characteristic in which it is not switched soon even if switch control is started, but changes with a certain amount of short time. A rise characteristic of the X-ray output and a fall characteristic thereof are different from each other. That is, when the X-ray output is raised and lowered, the way of a change in the X-ray output and the time necessary for the X-ray output to change differ. For this reason, even if the view angle range of the X-ray tube in which the X-ray output is set smaller than a normal level, and is arranged in a laterally symmetrical manner, the dose of X rays applied to the subject is not laterally symmetrical with each other. It is thus difficult to reduce the amount of radiation exposure to the tissue high in radiation sensitivity in a laterally well-balanced fashion.

With the foregoing in view, there has been a demand for an X-ray CT apparatus capable of reducing the amount of radiation exposure to a tissue high in radiation sensitivity in a laterally well-balanced fashion.

SUMMARY OF THE INVENTION

In one aspect, an X-ray CT apparatus including: is provided. The X-ray CT apparatus includes an X-ray tube which applies an X-ray onto a subject, a scan device which rotates the X-ray tube about the subject to perform an X-ray CT scan, a first control device which starts control for switching an X-ray output of the X-ray tube from a first level to a second level smaller than the first level upon execution of the X-ray CT scan when the X-ray tube is placed at a first view angle, and starts control for switching the X-ray output of the X-ray tube from the second level to the first level when the X-ray tube is placed at a second view angle different from the first view angle, and a second control device which controls the first view angle and the second view angle in such a manner that X-ray exposure dose reduced by setting the X-ray output of the X-ray tube smaller than the first level becomes even on right and left sides with respect to a reference view angle of the X-ray tube corresponding to the direction of the front of the subject.

In one embodiment, the second control device controls the first view angle and the second view angle in such a manner that an area of a region surrounded by a line of the first level and an actual line of the X-ray output becomes even on right and left sides with respect to the reference view angle on a graph indicative of a relationship between the view angle of the X-ray tube and the X-ray output thereof at the X-ray CT scan.

In one embodiment, the second control device controls the first view angle and the second view angle in such a manner that the position of gravity of the region or the center position thereof with respect to the direction of the view angle at the graph coincides with the reference view angle.

In one embodiment, the graph indicates a distribution of a tube current of the X-ray tube at the time that a tube voltage of the X-ray tube is held constant.

In another aspect, an X-ray CT apparatus is provided. The X-ray CY apparatus includes an X-ray tube which applies an X-ray onto a subject, a scan device which rotates the X-ray tube about the subject to perform an X-ray CT scan, a first control device which starts control for switching an X-ray output of the X-ray tube from a first level to a second level smaller than the first level upon execution of the X-ray CT scan when the X-ray tube is placed at a first view angle, and starts control for switching the X-ray output of the X-ray tube from the second level to the first level when the X-ray tube is placed at a second view angle different from the first view angle, and a second control device which controls the first view angle to be a view angle located short of a third view angle by a first angular width when two angles laterally symmetrical with respect to a reference view angle of the X-ray tube corresponding to the direction of the front of the subject are respectively set to the third view angle and a fourth view angle from the front side of the direction of rotation of the X-ray tube, and controls the second view angle to be a view angle located short of the fourth view angle by a second angular width smaller than the first angular width.

In one embodiment, the reference view angle is a view angle taken when the X-ray tube is located directly above the subject.

In one embodiment, the X-ray CT apparatus further includes an adjusting device which adjusts the reference view angle according to the operation of an operator.

In one embodiment, the X-ray CT apparatus further includes a detecting device which detects the posture of the subject, and an adjusting device which adjusts the reference view angle, based on the detected posture.

In one embodiment, the X-ray CT apparatus further includes a acquiring device which acquires an image taken when the subject is seen in an axial direction, wherein the detecting device detects a twist angle at which the direction of a body axis of the subject is taken as a central axis, based on the acquired image, and wherein the adjusting device adjusts the reference view angle according to the detected twist angle.

In one embodiment, the X-ray CT apparatus further includes an acquiring device which acquires an image taken when the subject is seen in an axial direction, wherein the detecting device detects lateral positions of the subject, based on the acquired image, and wherein the adjusting device adjusts the reference view angle according to the detected lateral positions.

In one embodiment, the X-ray CT apparatus further includes an acquiring device which acquires an image taken when the subject is seen in an AP direction, wherein the detecting device detects lateral positions of the subject, based on the acquired image, and wherein the adjusting device adjusts the reference view angle according to the detected lateral positions.

In one embodiment, the image taken when the subject is seen in the AP direction is an AP scout image, a PA scout image or a coronal tomographic image.

In one embodiment, the image taken when the subject is seen in the axial direction is an image obtained by a scan of an Nth rotation of the X-ray tube at a helical scan, and the adjusting device adjusts the reference view angle at a scan of an N+1th rotation of the X-ray tube at the helical scan.

In one embodiment, the image taken when the subject is seen in the axial direction is an image obtained by an axial scan at a first scan position, and the adjusting device adjusts the reference view angle at an axial scan at a second scan position close to the first scan position.

In one embodiment, the X-ray CT apparatus further includes a setting device which sets a rotational speed of the X-ray tube at the X-ray CT scan, wherein the second control device controls the first view angle and the second view angle as relative view angles from the reference view angle according to the set rotational speed of the X-ray tube.

In one embodiment, the X-ray CT apparatus further includes a selecting device which selects an imaging region of the subject, wherein the second control device controls the first view angle and the second view angle according to the selected imaging region.

In one embodiment, the X-ray CT apparatus further includes a storing device which stores therein candidates for the first view angle and the second view angle according to a combination of the rotational speed and the imaging region, wherein the second control device determines the candidates each associated with the combination of the set rotational speed and the selected imaging region as the first view angle and the second view angle.

In one embodiment, the X-ray output of the second level is an X-ray output obtained by multiplying the X-ray output of the first level by a prescribed coefficient smaller than 1.

In one embodiment, the X-ray output of the first level is an X-ray output which is determined by automatic exposure control and changes according to the view angle of the X-ray tube.

Here, the "view angle of the X-ray tube" defines the position of the X-ray tube in the direction of rotation thereof and is also called a gantry angle.

The "X-ray output of the first level" is an X-ray output determined by a scan condition not including such a condition that the amount of radiation exposure to a part of the subject is intentionally reduced. There are mentioned, for example, a prescribed X-ray output inputted by an operator upon a scan plan, an X-ray output varied according to the view angle of the X-ray tube, which is determined by automatic exposure control, etc. The X-ray output is determined according to the tube voltage and tube current of the X-ray tube.

According to the embodiments described herein, a first switch view angle and a second switch view angle at an exposure reduction scan can be controlled in such a manner that X-ray exposure dose becomes even on right and left sides in consideration of the characteristic of an X-ray output. The amount of radiation exposure to a tissue high in radiation sensitivity can be reduced in a laterally well-balanced fashion.

BRIEF DESCRIPTION OF THE DRAWINGS

FIG. 6 is a diagram showing one example illustrative of tube current switch parameters stored in advance.

DETAILED DESCRIPTION OF THE INVENTION

Embodiments of the present invention will hereinafter be described.

First Embodiment

Figure 1:
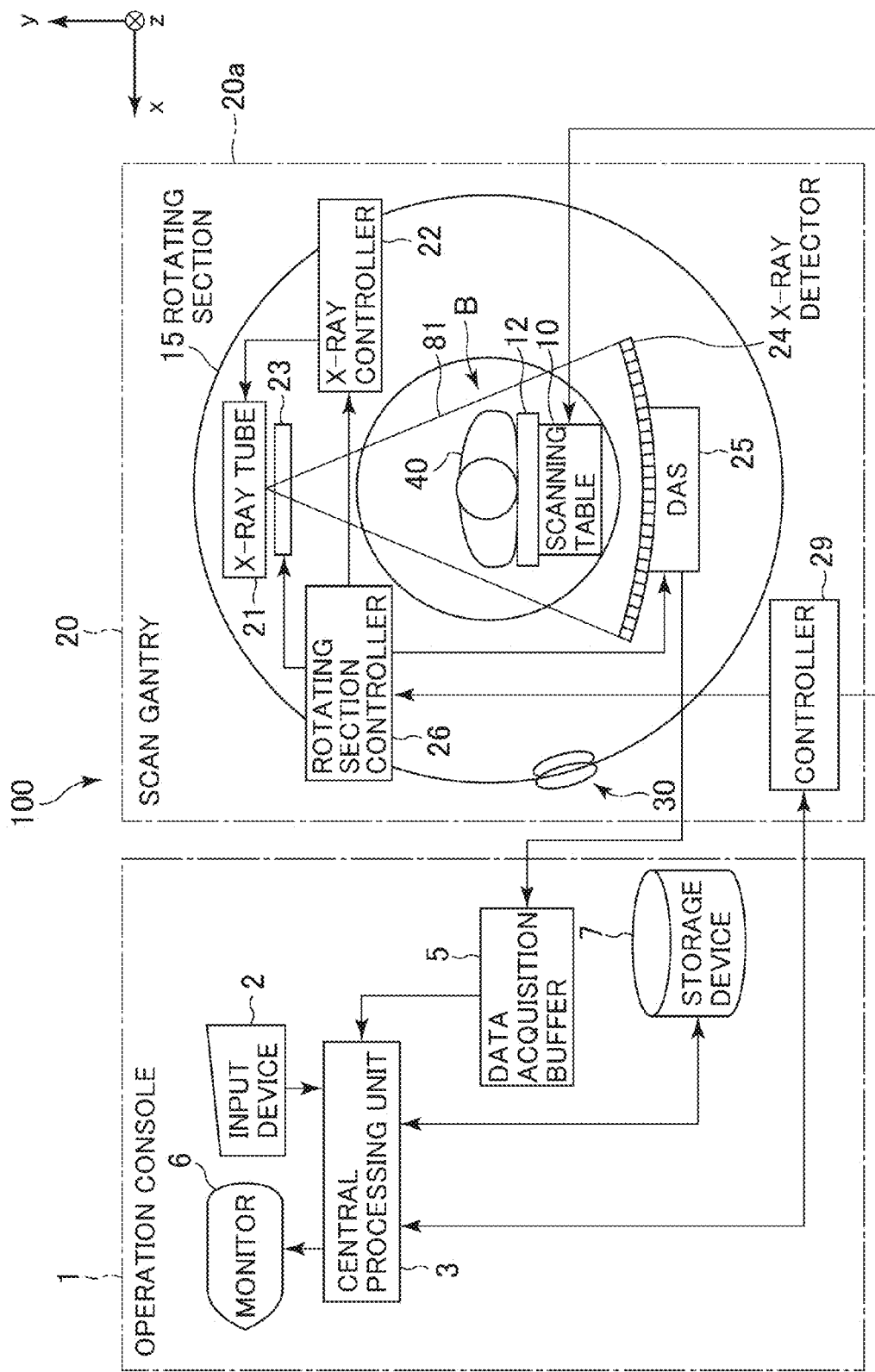
FIG. 1 is a diagram schematically showing a configuration of an X-ray CT apparatus according to a first embodiment.

FIG. 1 is a diagram schematically showing a configuration of an X-ray CT apparatus according to the present embodiment. The X-ray CT apparatus 100 is equipped with an operation console 1, a scanning table 10 and a scan gantry 20.

The operation console 1 is equipped with an input device 2 which accepts an input from an operator, a central processing unit 3 which performs control on respective parts for performing imaging of a subject, a data process for generating an image, etc., a data acquisition buffer 5 which acquires data obtained by the scan gantry 20, a monitor 6 which displays an image thereon, and a storage device 7 which stores a program, data and the like therein.

The scanning table 10 is equipped with a cradle 12 which conveys a subject 40 to an opening B of the scan gantry 20 with the subject 40 placed on the scanning table 10. The cradle 12 is moved up and down and linearly-moved horizontally by a motor built in the scanning table 10. Incidentally, assume now that the direction of a body axis of the subject 40, i.e., the direction of horizontal linear movement of the cradle 12 is a z direction, the vertical direction thereof is a y direction, and the horizontal direction thereof perpendicular to the z and y directions is an x direction. Also assume where the subject 40 is placed on the cradle 12 in a face-up state.

The scan gantry 20 has a rotating section 15, and a body section 20a which rotatably supports the rotating section 15. The rotating section 15 is equipped with an X-ray tube 21, an X-ray controller 22 which controls the X-ray tube 21, a collimator 23 which collimates an X-ray beam 81 generated from the X-ray tube 21, an X-ray detector 24 which detects the X-ray beam 81 that has penetrated through the subject 40, a data acquisition system (DAS) 25 which converts the output of the X-ray detector 24 into projection data and acquire the same therein, and a rotating section controller 26 which performs control of the X-ray controller 22, the collimator 23 and the DAS 25. The body section 20a has a control controller 29 which performs communication of a control signal or the like with the operation console 1 and the scanning table 10. The rotating section 15 and the body section 20a are electrically connected through a slip ring 30.

Figure 2:
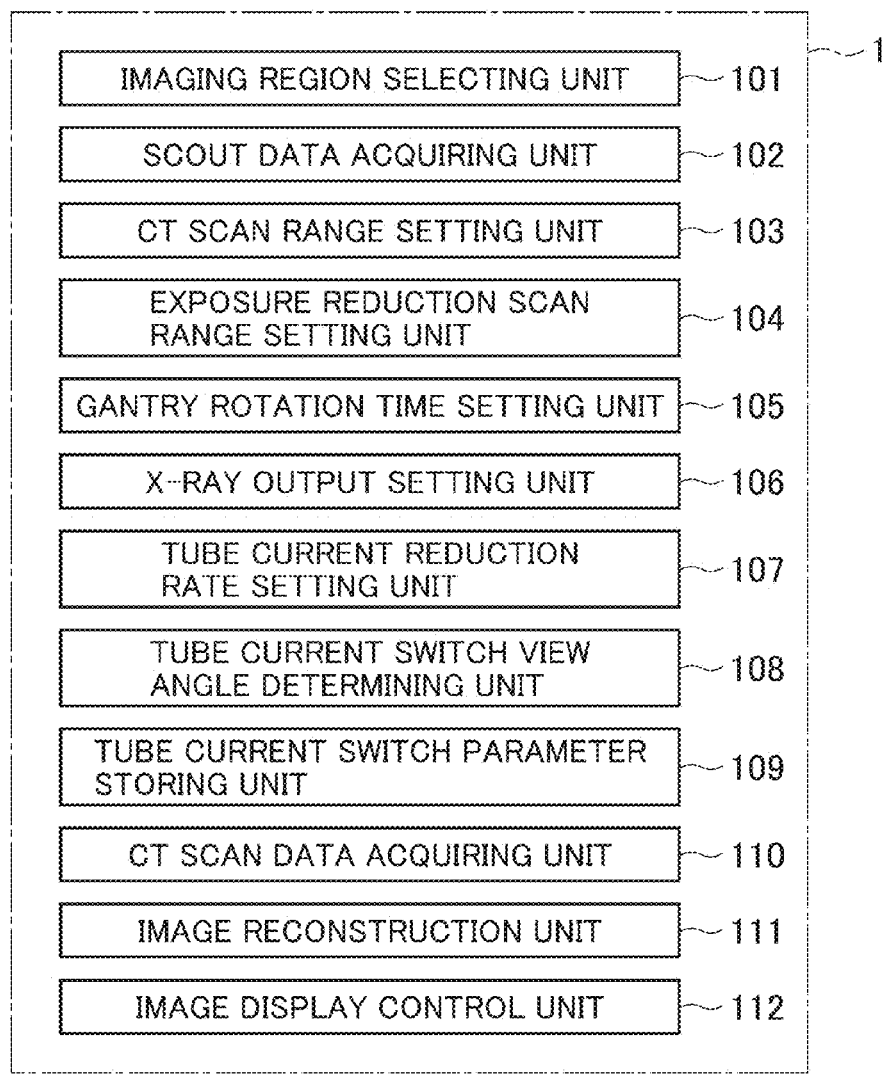
FIG. 2 is a functional block diagram of a section related to the execution of a scan by the X-ray CT apparatus according to the first embodiment.

FIG. 2 is a functional block diagram of a section related to the execution of a scan by the X-ray CT apparatus according to the present embodiment. As shown in FIG. 2, the X-ray CT apparatus according to the present embodiment includes an imaging region selecting unit (selecting device) 101, a scout data acquiring unit (acquiring device) 102, a CT scan range setting unit 103, an exposure reduction scan range setting unit 104, a gantry rotation time setting unit (setting device) 105, an X-ray output setting unit 106, a tube current reduction rate setting unit 107, a tube current switch view angle determining unit (second control device) 108, a tube current switch parameter storing unit (storing device) 109, a CT scan data acquiring unit (scan device, first control device) 110, an image reconstruction unit 111, and an image display control unit 112.

The imaging region selecting unit 101 selects a region to be imaged of the subject 40.

The scout data acquiring unit 102 sets a scout scan range of the subject 40. The scout scan range is a range in the z direction in which a scout scan is performed. The scout scan is a scan to be performed before an actual scan. There scout scan may include, for example, a scan for applying an X-ray beam having a dose lower than at the actual scan onto the subject while moving the subject or the scan gantry in the z direction with a view angle of the X-ray tube being held constant, thereby acquiring projection data. Further, the scout scan may include, for example, a helical scan using an X-ray beam having a dose much lower than at the actual scan. The scout data acquiring unit 102 controls the scanning table 10 and the scan gantry 20 to perform the scout scan on the set scout scan range RS, thereby acquiring scout data PS.

The CT scan range setting unit 103 sets a CT scan range at the actual scan. The CT scan range is a range in the z direction in which an X-ray CT scan is performed.

The exposure reduction scan range setting unit 104 sets an exposure reduction scan range at the actual scan. The exposure reduction scan range is a range of the CT scan range in the z direction, in which an exposure reduction scan is performed. The exposure reduction scan is a scan for setting a tube current of the X-ray tube lower than a normal first level L1 only during a period in which the X-ray tube 21 is placed in a prescribed view angle range, and thereby acquiring projection data.

The gantry rotation time setting unit 105 sets a gantry rotation time at the actual scan. The gantry rotation time is a parameter which defines a gantry rotational speed, i.e., a rotational speed of the X-ray tube 21. The gantry rotation time is a time required to rotate the X-ray tube 21 by one rotation.

The X-ray output setting unit 106 sets an X-ray output, i.e., a tube voltage and a tube current of the X-ray tube at the actual scan.

The tube current reduction rate setting unit 107 sets a tube current reduction rate k at the exposure reduction scan. The tube current reduction rate k is a reduction rate taken when the tube current of the X-ray tube is reduced from a tube current A1 of a first level L1 to a tube current of a second level L2. That is, the tube current of the second level L2 becomes $(1-k) \cdot A1$.

The tube current switch view angle determining unit 108 determines a first switch view angle $\theta 1$ and a second switch view angle $\theta 2$ at the exposure reduction scan. The first switch view angle $\theta 1$ is a view angle of the X-ray tube at which control for switching the tube current of the X-ray tube from the first level L1 to the smaller second level L2 is started. The second switch view angle $\theta 2$ is a view angle of the X-ray tube at which control for switching the tube current of the X-ray tube from the second level L2 to the first level L1 is started.

The tube current switch parameter storing unit 109 stores therein parameters about tube current switching.

The CT scan data acquiring unit 110 controls the scanning table 10 and the scan gantry 20 and performs a CT scan corresponding to the set CT scan range RC as an actual scan, thereby acquiring CT scan data PC. The CT scan data is also called "projection data".

The image reconstruction unit 111 performs an image reconstruction process such as a filter back projection process or the like, based on the CT scan data PC and thereby reconstructs tomographic images at respective positions as viewed in the z direction in the CT scan range RC.

The image display control unit 112 controls the monitor 6 to thereby display the image based on the scout data PS, the reconstructed image and other information on the screen of the monitor 6.

Thus, the operation of the X-ray CT apparatus according to the present embodiment will be explained.

Figure 3:
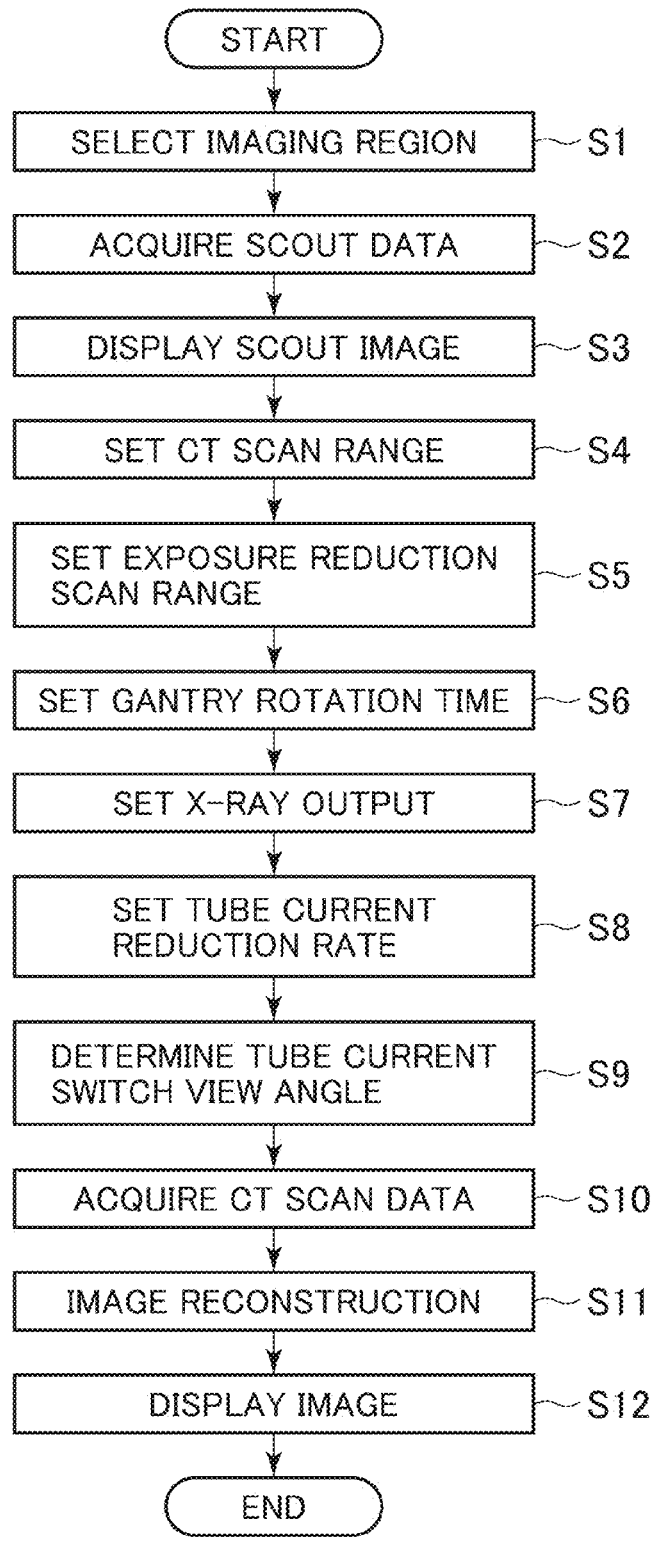
FIG. 3 is a flowchart showing a flow of operation of the X-ray CT apparatus according to the first embodiment.

FIG. 3 is a flowchart showing a flow of the operation of the X-ray CT apparatus according to the present embodiment.

At step S1, the imaging region selecting unit 101 selects an imaging or photographing region of the subject 40. In the present embodiment, the operator specifies one desired candidate from within candidates of a plurality of imaging regions. The imaging region selecting unit 101 selects the specified candidate as an imaging region B. The candidates for the imaging regions include, for example, a head region, a neck region, a chest region, an abdominal region, etc.

At step S2, the scout data acquiring unit 102 sets a scout scan range for the subject 40. In the present embodiment, the scout data acquiring unit 102 sets a prescribed range in the z direction, including the imaging region B selected at step S1 as a scout scan range RS according to the imaging region B. The scout data acquiring unit 102 controls the scanning table 10 and the scan gantry 20 and performs a scout scan on the set scout scan range RS, thereby acquiring scout data PS.

At step S3, the image display control unit 112 displays a scout image of the subject 40 on the screen of the monitor 6, based on the scout data PS acquired at step S2.

At step S4, the CT scan range setting unit 103 sets a CT scan range at the actual scan. In the present embodiment, the operator designates a desired range in the z direction on the scout image. The CT scan range setting unit 103 sets the designated range as the CT scan range RC.

Figure 4:
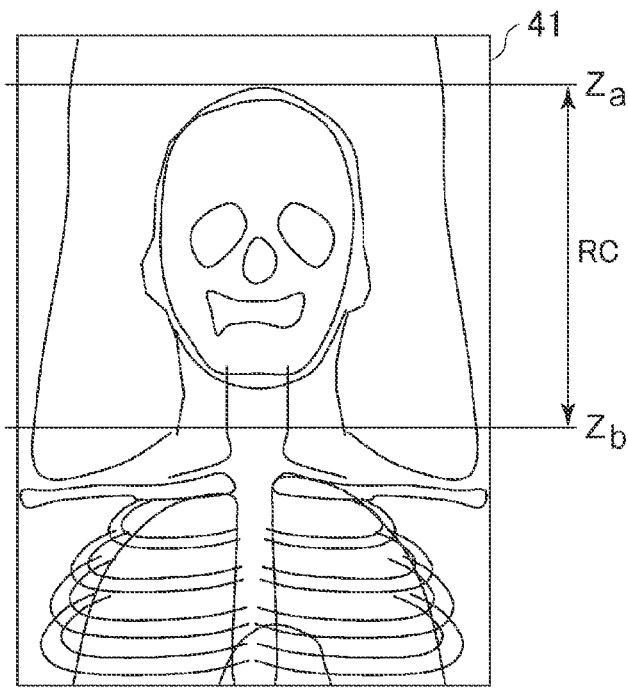
FIG. 4 is a diagram illustrating a set example of a CT scan range.

FIG. 4 is a diagram showing a set example of the CT scan range. In the present example, the operator designates a range for coordinates Za and Zb on a scout image 41 in an AP direction, indicative of the head region of the subject 40 and sets the range as a CT scan range RC.

At step S5, the exposure reduction scan range setting unit 104 sets an exposure reduction scan range at the actual scan. In the present embodiment, the operator specifies, on the displayed scout image, a range in the z direction including a tissue high in radiation sensitivity, which exists within the CT scan range RC. The exposure reduction scan range setting unit 104 sets the specified range in the z direction as an exposure reduction scan range RD.

Figure 5:
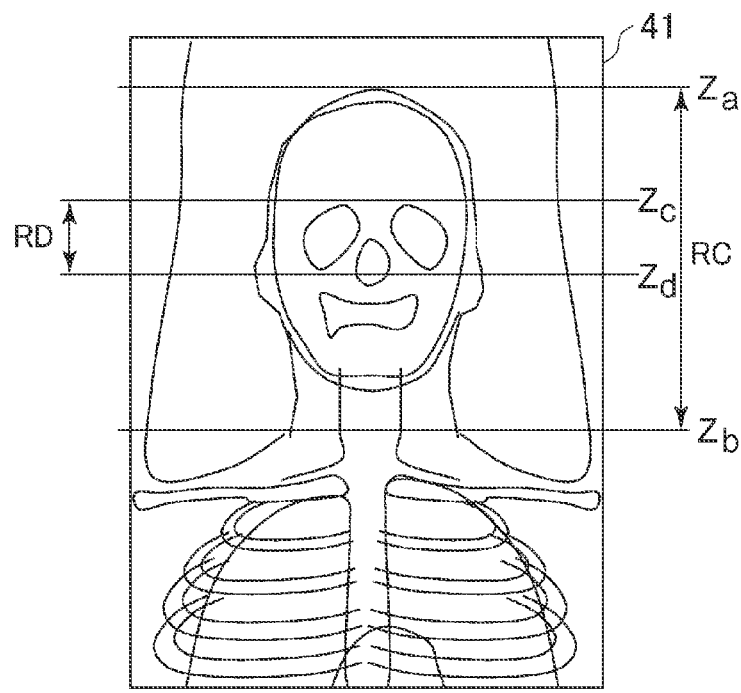
FIG. 5 is a diagram depicting a set example of an exposure reduction scan range.

FIG. 5 is a diagram showing a set example of an exposure reduction scan range. In the present example, the operator designates a range for coordinates Zc and Zd, including the crystalline lenses on the scout image 41 in the AP direction indicative of the head region of the subject 40 and sets the designated range as an exposure reduction scan range RD.

At step S6, the gantry rotation time setting unit 105 sets a gantry rotation time at the actual scan. In the present embodiment, the operator designates one desired candidates from within candidates of a plurality of gantry rotational speeds. The gantry rotation time setting unit 105 sets the designated candidate as a gantry rotational speed T. The candidates for the gantry rotational speeds may include, for example, 0.4 seconds, 0.6 seconds, 0.8 seconds, 1.0 seconds, etc.

At step S7, the X-ray output setting unit 106 sets an X-ray output of the X-ray tube at the actual scan. In the present embodiment, the operator inputs a desired tube voltage and a noise index of a reconstructed image. The X-ray output setting unit 106 sets the input tube voltage as a tube voltage V at the actual scan. The X-ray output setting unit 106 sets a tube current A1 of a first level L1 equivalent to the normal tube current at the actual scan by so-called automatic exposure control. The automatic exposure control determines a tube current A (Z) that changes depending on a z-direction coordinate Z of the X-ray tube 21 or a tube current A (Z, θ) that changes depending on a z-direction coordinate Z and a view angle θ of the X-ray tube 21, based on the acquired scout data PS and the input noise index NI. Thus, the X-ray output setting unit 106 sets the tube current A (Z) or the tube current A (Z, θ) as the tube current A1 of the first level L1. Incidentally, the X-ray output setting unit 106 may set the tube current inputted by the operator as the tube current A1 at the actual scan.

At step S8, the tube current reduction rate setting unit 107 sets a tube current reduction rate k at the exposure reduction scan. In the present embodiment, as shown in FIG. 6, candidates for tube current reduction rates are determined in advance for every imaging or photographing region and stored in the tube current switch parameter storing unit 109 in association with one another. The tube current reduction rate setting unit 107 sets a candidate for a tube current reduction rate associated with the imaging region B selected at step S1, as the tube current reduction rate k.

The optimum value for the tube current reduction rate k varies according to the type of tissue high in radiation sensitivity, which is intended for radiation exposure reduction. However, the type of tissue high in radiation sensitivity intended for radiation exposure reduction can be substantially specified by the imaging region. Thus, if the tube current reduction rate k is set in the above-described manner, then the optimum tube current reduction rate can be set according to the tissue high in radiation sensitivity, which is included in the imaging region. Since the tissue high in radiation sensitivity becomes a crystal lens/thyroid when the imaging region is of the head/neck region, for example, the tube current reduction rate k is assumed to be 0.6 (60%), for example. Since the tissue high in radiation sensitivity becomes lacteal glands when the imaging region is of the chest region, for example, the tube current reduction rate k is assumed to be 0.4 (40%), for example. Since the tissue high in radiation sensitivity becomes a generative organ when the imaging region is of the abdominal region, for example, the tube current reduction rate k is assumed to be 0.5 (50%), for example. Incidentally, the tube current reduction rate setting unit 107 may set the reduction rate designated by the operator as the tube current reduction rate k.

At step S9, the tube current switch view angle determining unit 108 determines a first switch view angle θ1 and a second switch view angle θ2 at the exposure reduction scan. In the present embodiment, as shown in FIG. 6, the tube current switch parameter storing unit 109 stores therein a table in which candidates for the first switch view angle θ1 and the second switch view angle θ2 are associated with each other every combination of the imaging region and the gantry rotation time. The tube current switch view angle determining unit 108 determines candidates associated with the combination of the imaging region B selected at step S1 and the gantry rotation time T set at step S6, as the first switch view angle A1 and the second switch view angle θ2 by referring to the table.

A description will now be made of how to determine the table.

Figure 7:
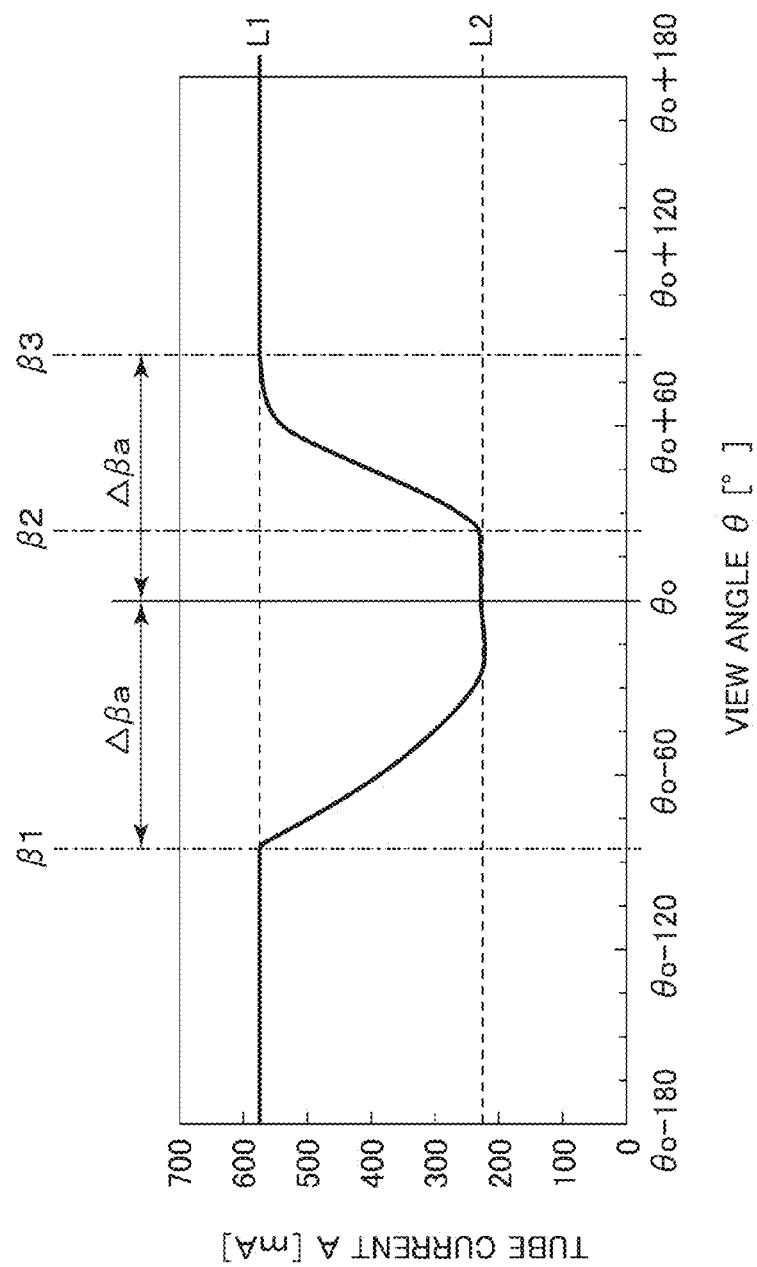
FIG. 7 is an example of a graph showing the relationship between a view angle and a tube current of an X-ray tube at a general exposure reduction scan.

FIG. 7 is an example of a graph indicative of the relationship between a view angle and a tube current of the X-ray tube at the exposure reduction scan. In the example of the graph, assume that the tube voltage is a prescribed constant voltage and the normal level of the tube current is a first level L1, and that a control for switching the tube current from the first level L1 to a second level L2 at a view angle β1 has been started. Further, control for switching the tube current from the second level L2 to the first level L1 at a view angle β2 is started, and the tube current is returned to the first level L1 at a view angle β3. In the example of the graph as well, the tube current reduction view angle range is set so as to be laterally symmetrical with respect to a reference view angle θo of the X-ray tube, based on the idea of the conventional general exposure reduction scan. The tube current reduction view angle range is a view angle range of the X-ray tube at which the tube current becomes smaller than the first level L1 corresponding to the normal level. In the example of the graph, the tube current reduction view angle range corresponds to a range from the view angle β1 to the view angle β3. The reference view angle is a view angle of the X-ray tube corresponding to the front direction (AP direction) of the subject and corresponds to the right-left center of the subject.

As is understood from this graph, a rise characteristic of the tube current of the X-ray tube and its fall characteristic differ from each other. That is, the way of changes in the tube current and the time necessary for the tube current to change differ when the tube current rises and falls. For this reason, the changes in the tube current become asymmetrical with respect to the left and right of the subject, so that the amounts of reductions in the radiation exposure of the right and left sides of the subject get out of balance.

Thus, in the present embodiment, the first switch view angle θ1 and the second switch view angle θ2 are determined in such a manner that X-ray exposure dose reduced by setting the tube current of the X-ray tube smaller than the first level L1, i.e., the amount of a reduction in radiation exposure becomes even on right and left sides with respect to the reference view angle θo to prevent such imbalance of the amount of the reduction in exposure. Thus, the first switch view angle θ1 and the second switch view angle θ2 are relative angles as viewed from the reference view angle θo.

For example, one tissue high in radiation sensitivity is first specified as a target for exposure reduction. The first and second levels L1 and L2 of the tube current and the width Δβw of the tube current reduction view angle range, which are considered to be suitable for the specified tissue, are determined.

Figure 8:
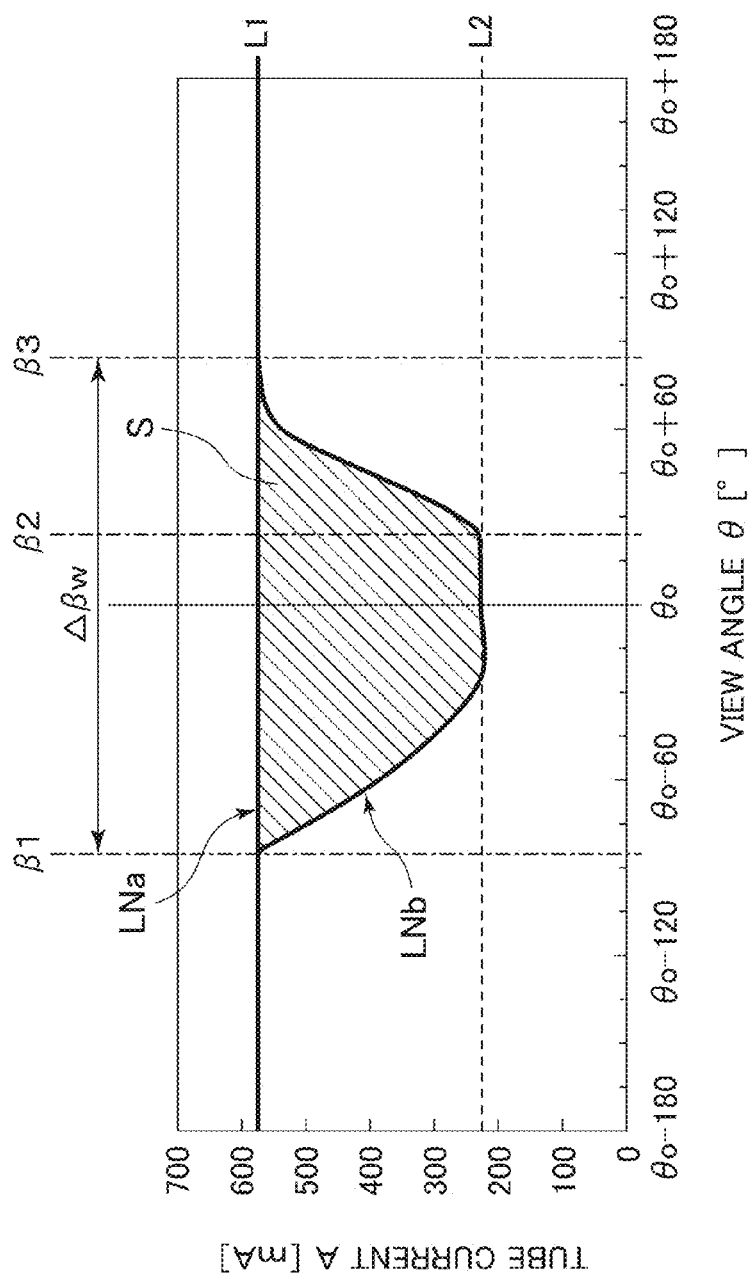
FIG. 8 is an example of a graph showing the relationship between a view angle and a tube current of the X-ray tube, which are determined by actual measurement or simulation.

Next, a graph indicative of the relationship between a view angle θ and a tube current of the X-ray tube is determined by actual measurement or simulation as shown in FIG. 8 with respect to the exposure reduction scan based on the first and second levels L1 and L2 of the tube current and the width Δβw of the tube current reduction view angle range both determined in this way.

Next, a tube current reduction region S surrounded by a line LNa of a first level L1 and a line LNb of an actual tube current is specified on the determined graph as shown in FIG. 8. The line LNb of the actual tube current is shifted in the direction of a view angle θ of the X-ray tube in such a manner that the area of the tube current reduction region S is held substantially in a laterally uniform manner with respect to a reference view angle θo. That is, a view angle β1 at which control for switching the tube current from the first level L1 to the second level L2 is started, and a view angle β2 at which control for switching the tube current from the second level L2 to the first level L1 is started, are shifted by a predetermined view angle Δβb.

Figure 9:
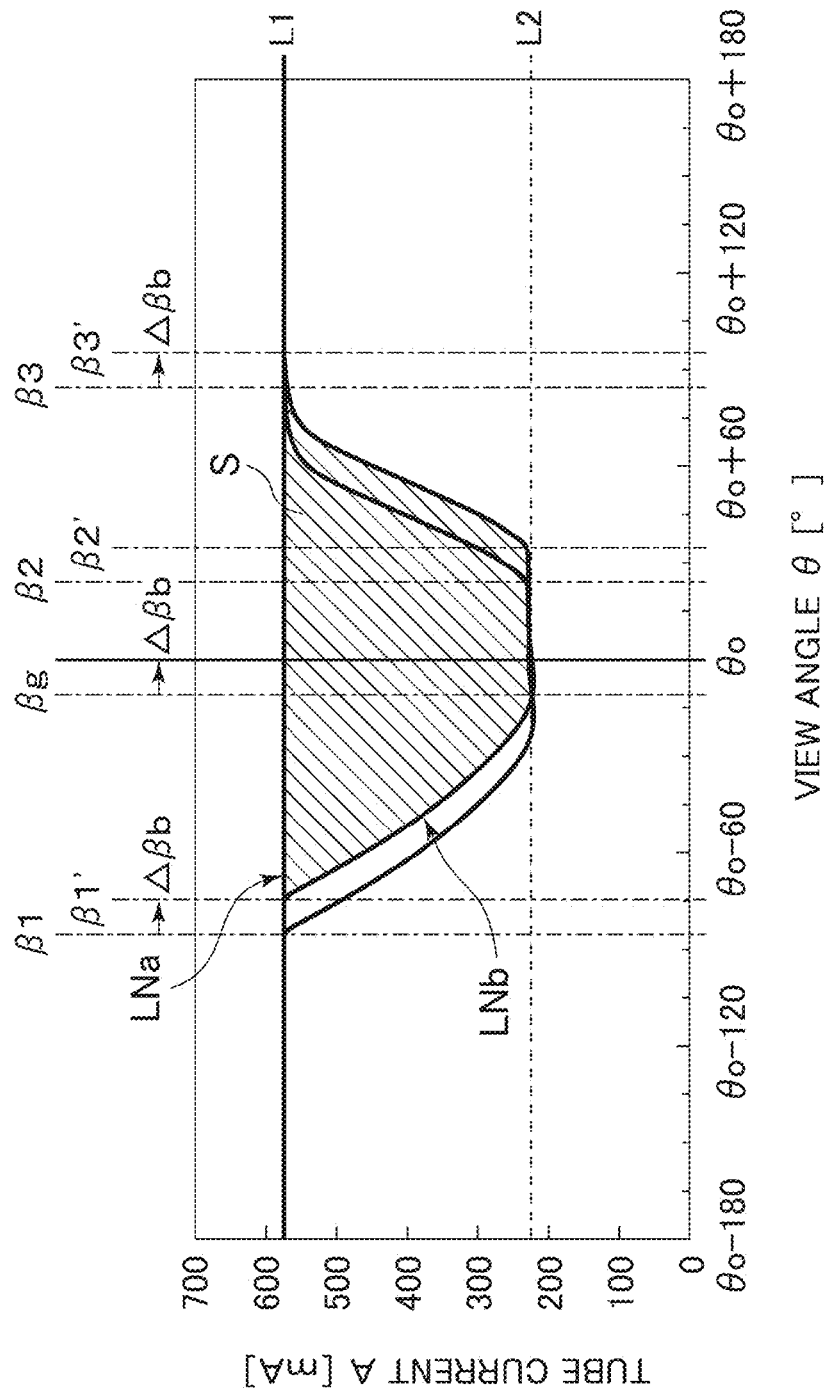
FIG. 9 is a diagram for describing a first method of determining a first switch view angle and a second switch view angle.
Figure 10:
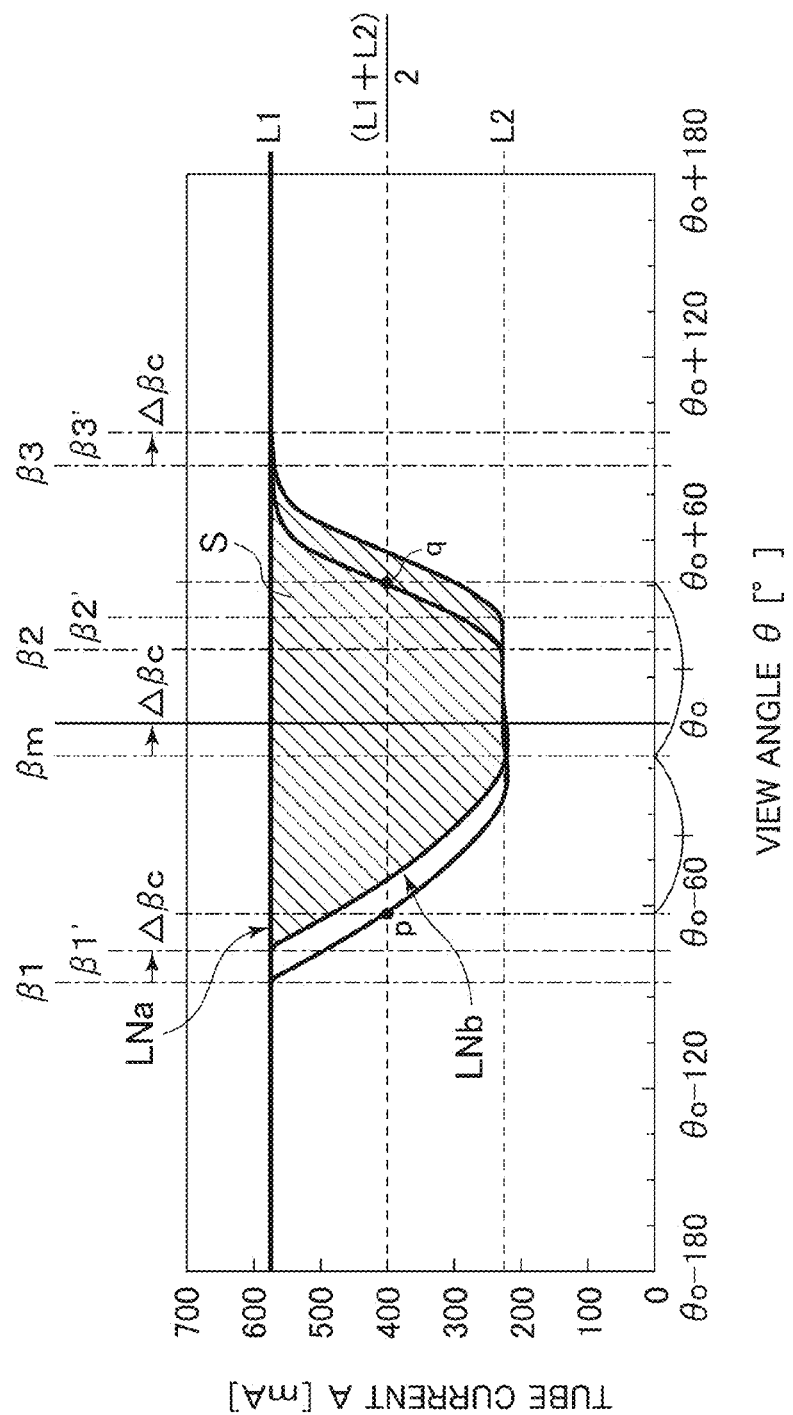
FIG. 10 is a diagram for describing a second method of determining a first switch view angle and a second switch view angle.

As a concrete method for performing such a shift, as shown in FIG. 9, for example, a view angle β1 and a view angle β2 are shifted in such a manner that the position of the center of gravity βg of the tube current reduction region S at the above graph with respect to the direction of a view angle θ coincides with a reference view angle θo. As shown in FIG. 10, for example, a view angle β1 and a view angle β2 are shifted in such a manner that a center position βm of the tube current reduction region S at the above graph with respect to the direction of a view angle θ coincides with a reference view angle θo. The center position βm is a position that corresponds to a midpoint of a line segment pq when a point that reaches a middle level between a first level L1 and a second level at the rise of a tube current is p, and a point that reaches a middle level therebetween at the fall of the tube current, is q.

Thereafter, a view angle β1' subsequent to the shifting of the view angle β1, and a view angle β2' subsequent to the shifting of the view angle β2 are respectively assumed to be candidates for the first switch view angle θ1 and the second switch view angle θ2.

Incidentally, the optimum values of both the first level L1 of the tube current and the second level L2 thereof, and the optimum value of the width Δβw of the tube current reduction view angle range differ from each other according to the type of tissue high in radiation sensitivity, which is target for exposure reduction. The type of tissue high in exposure sensitivity is substantially specified according to the type of imaging region. A curve of a change in tube current with respect to the view angle θ of the X-ray tube at the exposure reduction scan changes depending on the rotational speed of the X-ray tube, i.e., the gantry rotation time.

Thus, the candidates for the first switch view angle θ1 and the second switch view angle θ2 are determined in accordance with the above procedure for every possible combination of the imaging region and the gantry rotation time. Consequently, such a table as shown in FIG. 6 is determined.

Incidentally, in the present embodiment, the reference view angle θo is assumed to be a view angle 0°, i.e., a view angle at which the X-ray tube located directly above the subject.

At step S10, the CT scan data acquiring unit 110 controls the scanning table 10 and the scan gantry 20 to perform a CT scan on the set CT scan range RC as the actual scan, thereby acquiring CT scan data PC. In the present embodiment, a helical scan is assumed as an X-ray CT scan, but may be an axial scan. The gantry rotation time and the tube voltage of the X-ray tube at the actual scan are respectively controlled to be the set gantry rotation time T and tube voltage V. The tube current of the X-ray tube at the actual scan is controlled to be always the tube current A1 that is the first level L1, when other than the exposure reduction scan. In the case of the exposure reduction scan, the tube current of the X-ray tube is controlled to be normally the tube current A1 that is the first level L1. When, however, the X-ray tube is placed at the first switch view angle θ1, control for switching the tube current from the tube current A1 that is the first level L1 to the tube current (1−k)·A1 that is of the second level L2, is started. When the X-ray tube is placed at the second switch view angle θ2, control for switching the tube current from the tube current (1−k)·A1 that is of the second level L2 to the tube current A1 that is of the first level L1, is started.

At step S11, the image reconstruction unit 111 performs an image reconstruction process such as a filter backprojection process, based on the CT scan data PC acquired at step S10 to reconstruct a tomographic image at each position as viewed in the z direction in the CT scan range RC.

At step S12, the image display control unit 112 displays the tomographic image reconstructed at step S11 on the screen of the monitor 6.

According to such a first embodiment, the first switch view angle and the second switch view angle at the exposure reduction scan can be controlled in such a manner that X-ray exposure dose becomes even on right and left sides in consideration of the characteristic of an X-ray output, and the amount of radiation exposure to a tissue high in radiation sensitivity can be reduced in a laterally well-balanced fashion.

Second Embodiment

Figure 11:
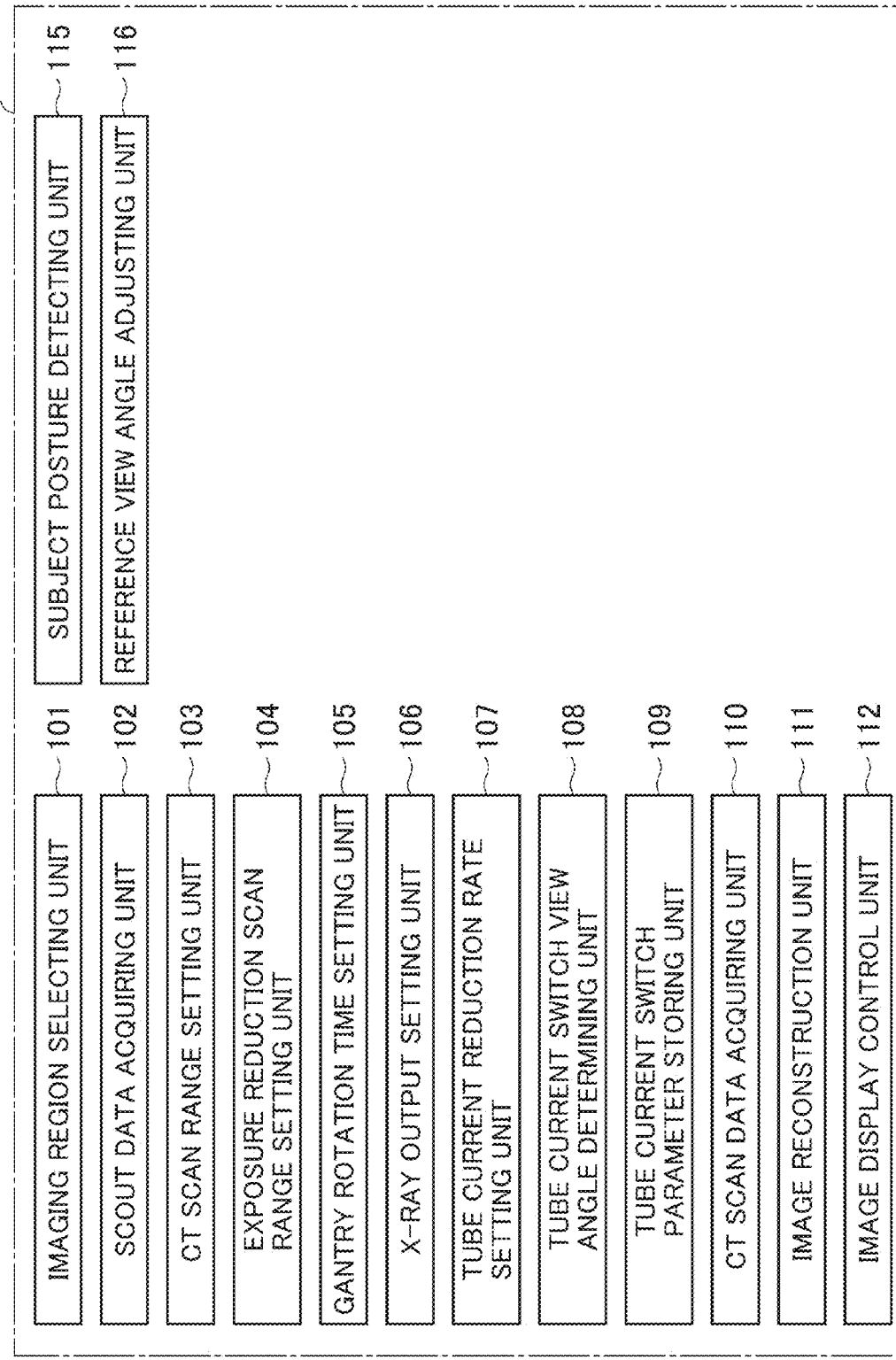
FIG. 11 is a functional block diagram of a section related to the execution of a scan by an X-ray CT apparatus according to a second embodiment.

FIG. 11 is a functional block diagram of a section related to the execution of a scan by an X-ray CT apparatus according to a second embodiment.

The X-ray CT apparatus according to the second embodiment is further equipped with a subject posture detecting unit 115 and a reference view angle adjusting unit 116 as compared with the first embodiment.

The subject posture detecting unit 115 detects the posture of a subject.

The reference view angle adjusting unit 116 adjusts a reference view angle θo, based on the detected posture.

First Adjustment Example

A first adjustment example of a reference view angle will be explained.

Figure 12:
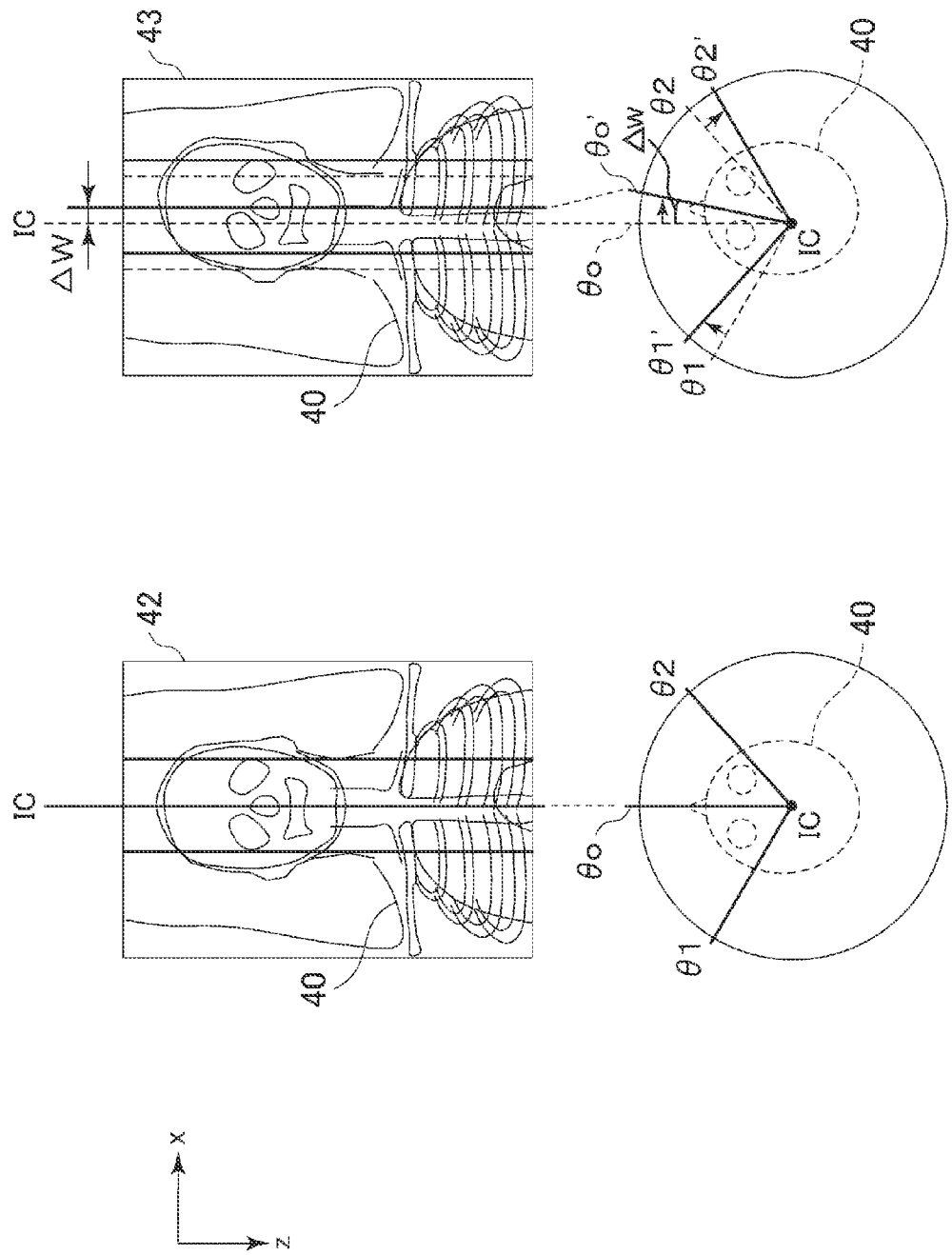
FIG. 12 is a diagram for describing a first adjustment example of a reference view angle in the second embodiment.

FIG. 12 is a diagram for explaining the first adjustment example of the reference view angle. In the first adjustment example, the right and left positions of an imaging region are detected based on an AP-direction image of the subject, which is obtained from scout image, to thereby adjust the reference view angle θo before an actual scan. The AP-direction image is an image obtained when the subject is viewed in an AP direction or a PA direction.

The scout data acquiring unit 102 acquires scout data PS of the subject by an AP scout scan, a PA scout scan or a low dose helical scan at which the rotation of the an X-ray tube is stopped.

The subject posture detecting unit 115 reconstructs the AP-direction image, based on the scout data PS. The AP-direction image is, for example, an AP scout image of the subject or a coronal image by an MPR process.

The subject posture detecting unit 115 detects the position of the subject in the horizontal direction, i.e., the x direction, based on the AP-direction image and thereby detects the amount of a shift from an iso-center IC of a body axis (center line) of the imaging region. The iso-center IC is the center of rotation of the X-ray tube 21.

The reference view angle adjusting unit 116 adjusts the reference view angle θo according to the detected amount of shift in the x direction, of the imaging region.

Each of images 42 and 43 shown in FIG. 12 is one example of an AP-direction image at the time that the imaging region is assumed to be a head region. The reference view angle adjusting unit 116 adjusts the reference view angle θo to 0° when the amount of a shift in the x direction, of the head region is 0 as indicated by the image 42 of FIG. 12, for example. When the amount of the shift in the x direction, of the head region is +Δw as indicated by the image 43 of FIG. 12, for example, the reference view angle adjusting unit 116 adjusts the reference view angle θo to θo' that is +Δw° corresponding to +ΔW. With this adjustment, the first switch view angle θ1 and the second switch view angle θ2 also become θ1' and θ2' shifted by +Δw° as compared with when the reference view angle θo is 0°.

Second Adjustment Example

A second adjustment example of a reference view angle will be explained.

Figure 13:
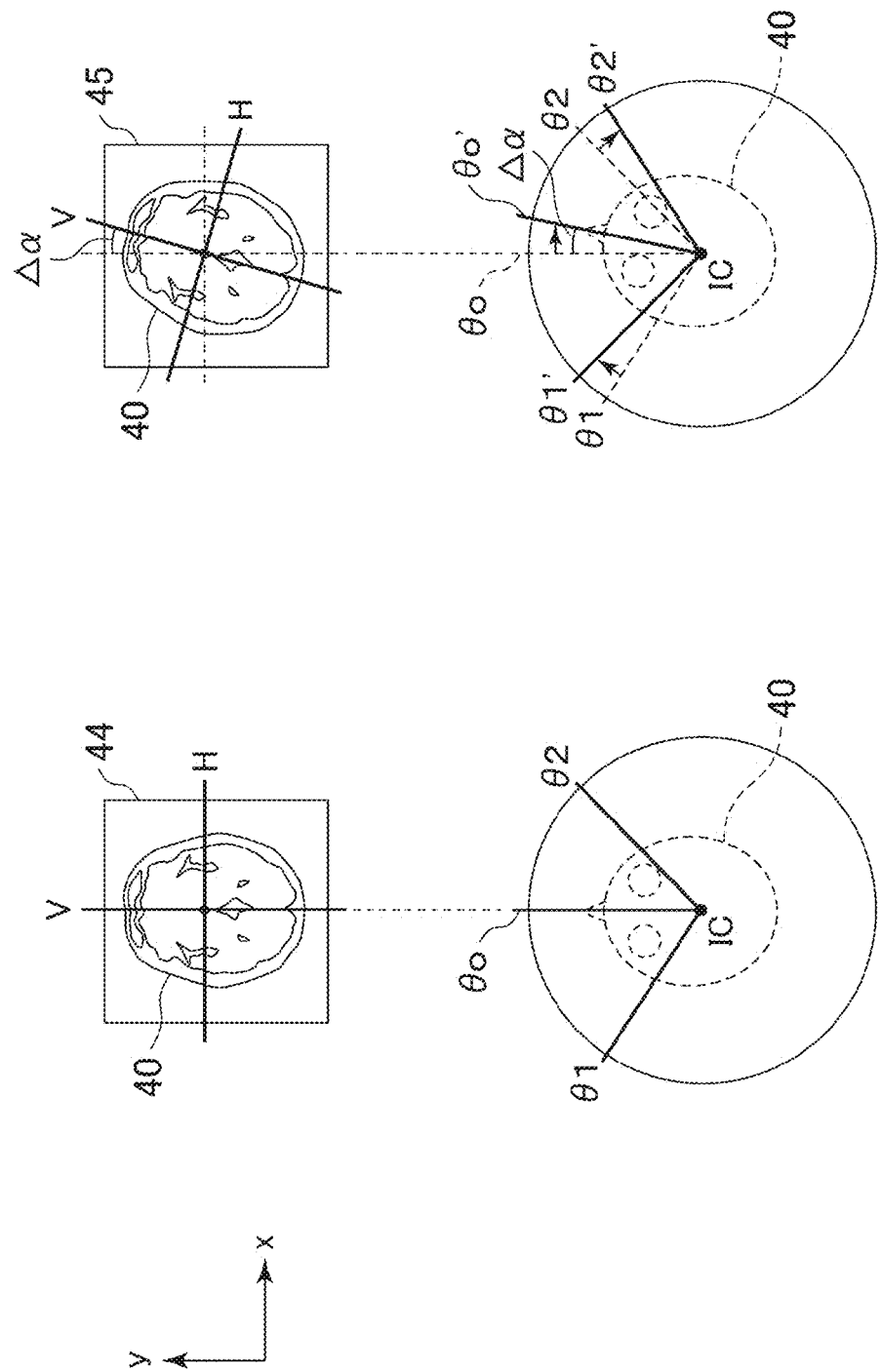
FIG. 13 is a diagram for describing a second adjustment example of the reference view angle in the second embodiment.

FIG. 13 is a diagram for describing the second adjustment example of the reference view angle. In the second adjustment example, a twist angle of an imaging region is detected based on an axial image of a subject obtained from scout data to thereby adjust a reference view angle θo. The axial image is an image obtained when the subject is seen in the axial direction.

The scout data acquiring unit 102 acquires scout data PS of the subject by the low dose helical scan.

The subject posture detecting unit 115 reconstructs an axial image lying in an exposure reduction scan range RD, based on the scout data PS. This axial image is, for example, a tomographic image in which an xy plane is assumed to be a cross-section.

The subject posture detecting unit 115 detects a twist angle of an imaging region, based on the axial image. This twist angle is a rotation angle of an imaging region in which the direction of a body axis of a subject, i.e., the z direction is taken as a central axis. When the front side of the imaging region faces in the y direction, the twist angle is assumed to be 0°.

The reference view angle adjusting unit 116 adjusts the reference view angle θo according to the detected twist angle of imaging region.

Each of images 44 and 45 shown in FIG. 13 is one example of an axial image taken when the imaging region is assumed to be a head region. When the twist angle of the head region is 0° as indicated by the image 44 of FIG. 13, for example, the reference view angle adjusting unit 116 adjusts the reference view angle θo to 0°. When the twist angle of the head region is +Δα° as indicated by the image 45 of FIG. 13, for example, the reference view angle adjusting unit 116 adjusts the reference view angle θo to θo' that is +Δα°. With this adjustment, the first switch view angle θ1 and the second switch view angle θ2 also become θ1' and θ2' shifted by +Δα° as compared with when the reference view angle θo is 0°.

Third Adjustment Example

A third adjustment example of a reference view angle will be described.

Figure 14:
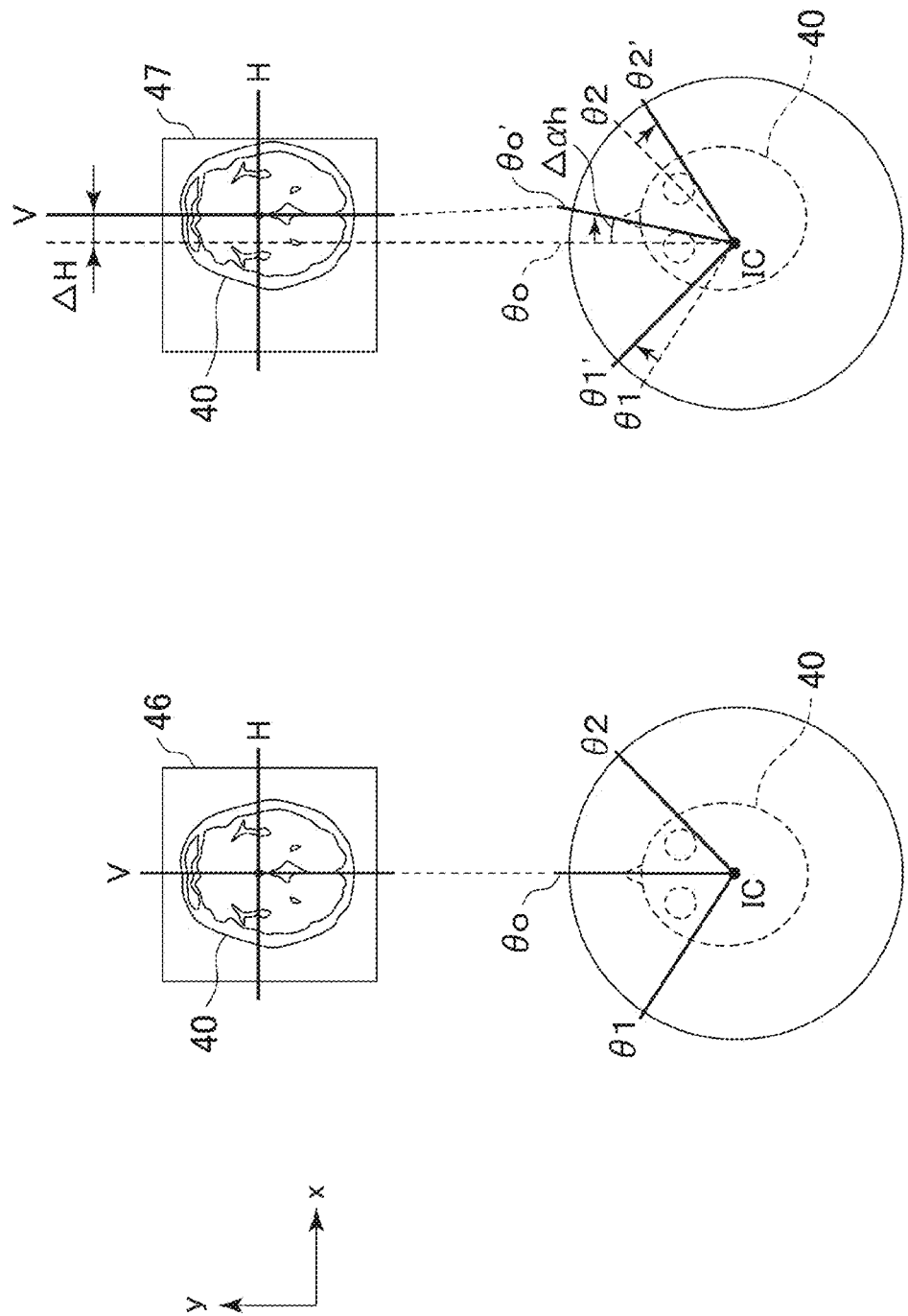
FIG. 14 is a diagram for describing a third adjustment example of the reference view angle in the second embodiment.

FIG. 14 is a diagram for describing the third adjustment example of the reference view angle. In the third adjustment example, the right and left positions of an imaging region are detected based on an axial image of a subject, which is obtained from scout data to thereby adjust a reference view angle θo.

The scout data acquiring unit 102 acquires scout data PS of the subject by the low dose helical scan.

The subject posture detecting unit 115 reconstructs an axial image lying in an exposure reduction scan range RD, based on the scout data PS. This axial image is, for example, a tomographic image in which an xy plane is assumed to be a cross-section.

The subject posture detecting unit 115 detects the position of the imaging region in the horizontal direction, i.e., the x direction, based on the axial image and thereby detects the amount of a shift from an iso-center IC of a center line of the imaging region.

The reference view angle adjusting unit 116 adjusts the reference view angle θo according to the detected amount of shift in the x direction, of the imaging region.

Each of images 46 and 47 shown in FIG. 14 is one example of an axial image at the time that the imaging region is assumed to be a head region. The reference view angle adjusting unit 116 adjusts the reference view angle θo to 0° when the amount of a shift in the x direction, of the head region is 0 as indicated by the image 46 of FIG. 14, for example. When the amount of the shift in the x direction, of the head region is +ΔH as indicated by the image 47 of FIG. 14, the reference view angle adjusting unit 116 adjusts the reference view angle θo to θo' that becomes +Δαh° corresponding to +ΔH. With this adjustment, a first switch view angle θ1 and a second switch view angle θ2 also become θ1' and θ2' shifted by +Δαh° as compared with when the reference view angle θo is 0°.

According to such first to third adjustment examples of the second embodiment, even when the shift of the subject in the horizontal direction and the twist with the body axis taken as the central axis have occurred, the reference view angle can be adjusted in correspondence with the shift and the twist. Thus, the amount of a reduction in radiation exposure can be brought into balance at the right and left halves of the subject.

Fourth Adjustment Example

A fourth adjustment example of a reference view angle will be explained.

Figure 15:
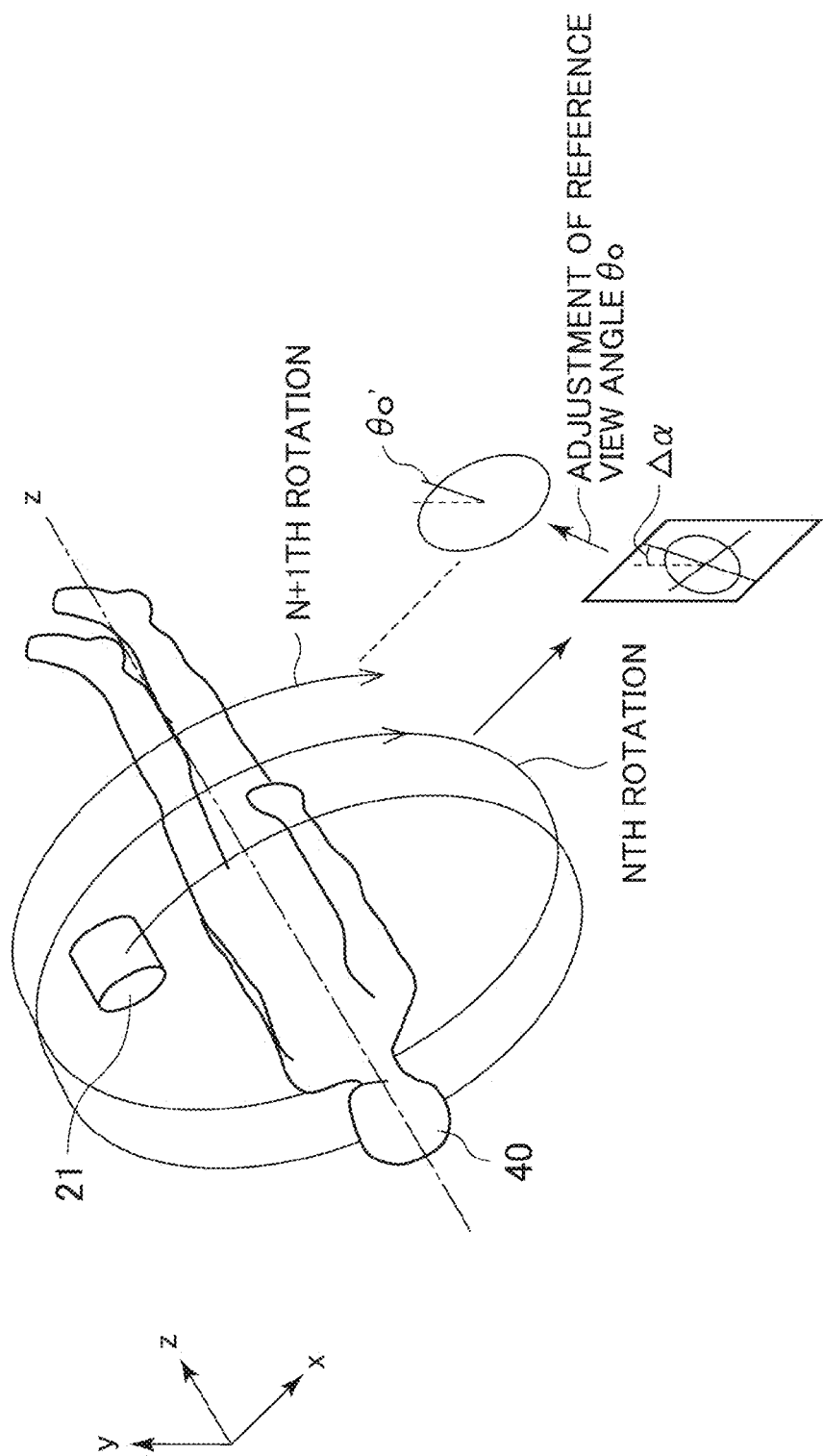
FIG. 15 is a diagram for describing a fourth adjustment example of the reference view angle in the second embodiment.

FIG. 15 is a diagram for describing the fourth adjustment of the reference view angle. In the fourth adjustment example, a reference view angle θo is adjusted while a helical scan is being performed.

The CT scan data acquiring unit (acquiring device) 111 performs a helical scan relatively small in helical chip (for example, 1 or less in IEC standards) to thereby acquire continuous CT scan data.

The subject posture detecting unit 115 reconstructs an axial image lying within an exposure reduction scan range RD, based on CT scan data CD by a scan at an Nth rotation of the X-ray tube.

The subject posture detecting unit 115 detects the amount of a shift in an x direction, of an imaging region and a twist angle with a z direction taken as a central axis, based on the axial image.

The reference view angle adjusting unit 116 adjusts a reference view angle θo at a scan corresponding to an N+1th rotation of the X-ray tube to θo', according to the detected amount of shift and twist angle of the imaging region in the x direction.

Fifth Adjustment Example

A fifth adjustment example of a reference view angle will be explained.

Figure 16:
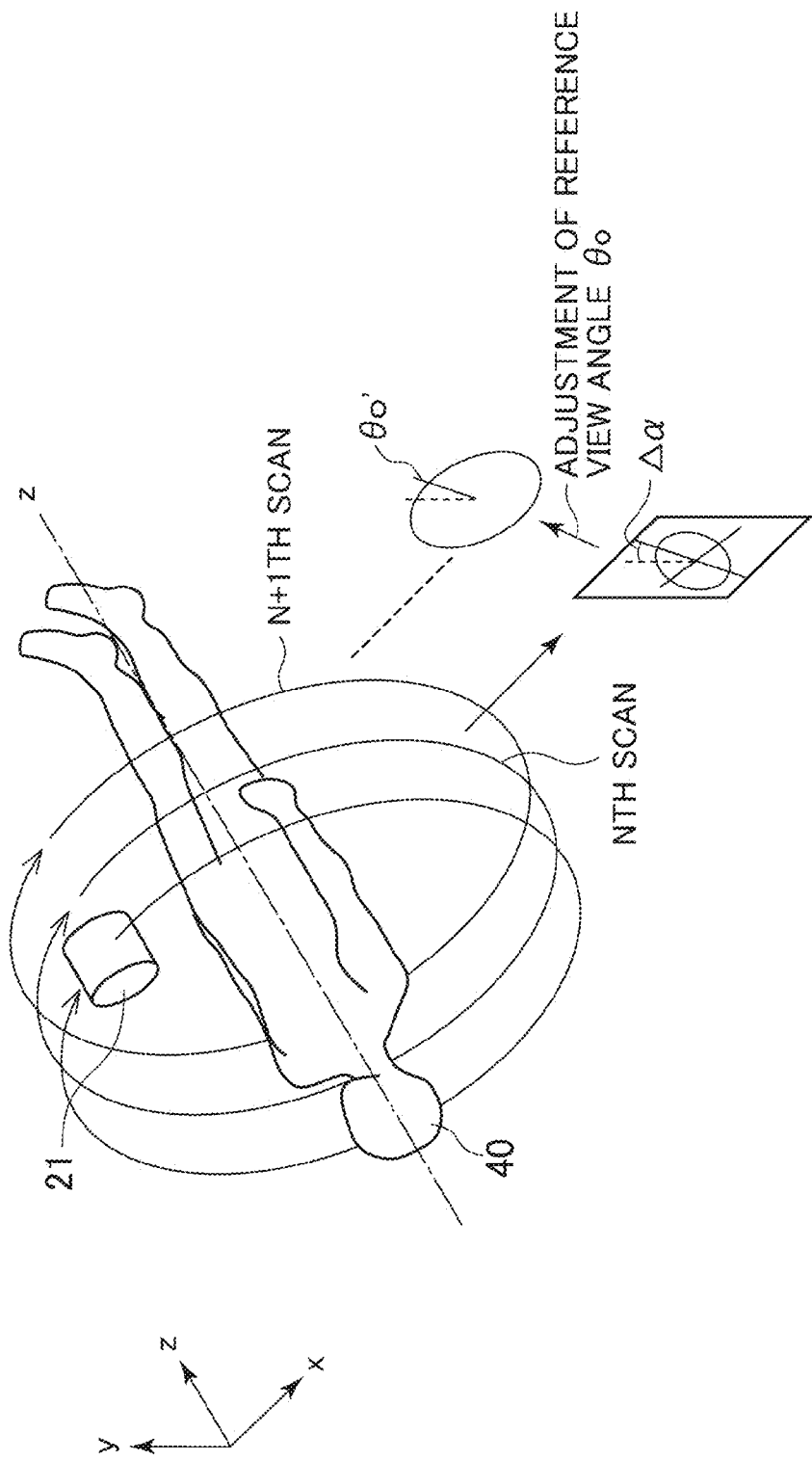
FIG. 16 is a diagram for describing a fifth adjustment example of the reference view angle in the second embodiment.

FIG. 16 is a diagram for explaining the fifth adjustment example of the reference view angle. In the fifth adjustment example, a reference view angle θo is adjusted while a continuous axial scan is being performed plural times.

The CT scan data acquiring unit 111 continuously performs an axial scan at a plurality of scan positions arranged adjacent to each other in the z direction to thereby acquire CT scan data at the scan positions.

The subject posture detecting unit 115 reconstructs an axial image lying in an exposure reduction scan range RD, based on CT scan data CD based on an Nth axial scan. This axial image is, for example, a tomographic image in which an xy plane is assumed to be a cross-section.

The subject posture detecting unit 115 detects the amount of a shift of an imaging region in its x direction and a twist angle with the z direction taken as a central axis, based on the axial image.

The reference view angle adjusting unit 116 adjusts a reference view angle θo at an N+1th axial scan to θo' according to the detected x-direction shift in the imaging region and its twist angle.

According to such fourth and fifth adjustment examples of the second embodiment, even when the shift of the subject in the horizontal direction and the twist with its body axis taken as the central axis change with respect to the z direction, the reference view angle can be adjusted following the changes.

Incidentally, the embodiments of the invention are not limited to the above embodiments specifically described herein. Various modifications can be made within the scope without departing from the spirit and scope of the invention.

In the above embodiment, for example, the tube current switch view angle determining unit 108 has decided the first switch view angle θ1 and the second switch view angle θ2 by referring to the table, but may determine and decide these by prescribed operational equations.

In the above embodiment as well, for example, the CT scan range setting unit 103 and the exposure reduction scan range setting unit 104 set the CT scan range and the exposure reduction scan range, based on the ranges instructed by the operator, but may automatically set them from the result of analysis of the scout image.

Further, in the above embodiment, for example, the subject 40 is assumed to be placed on the cradle 12 in the face-up state. However, there is also considered an embodiment in which the subject 40 is placed on the cradle 12 in a face-down state.

Further, the various candidates and the table in the above embodiment are illustrated by way of example, but are not limited by or to these.

The invention claimed is:

1. An X-ray CT apparatus comprising:
an X-ray tube configured to apply an X-ray onto a subject;
a scan device configured to rotate the X-ray tube about the subject to perform an X-ray CT scan;
a first control device configured to switch an X-ray output of the X-ray tube from a first level to a second level smaller than the first level during the X-ray CT scan when the X-ray tube is placed at a first view angle, and configured to switch the X-ray output of the X-ray tube from the second level to the first level when the X-ray tube is placed at a second view angle different from the first view angle; and
a second control device configured to set the first view angle and the second view angle such that an X-ray exposure dose reduced by setting the X-ray output of the X-ray tube smaller than the first level becomes even on right and left sides with respect to a reference view angle of the X-ray tube corresponding to a direction of a front of the subject.

2. The X-ray CT apparatus according to claim 1, wherein the second control device is configured to set the first view angle and the second view angle such that an area of a region surrounded by a line of the first level and an actual line of the X-ray output becomes even on right and left sides with respect to the reference view angle on a graph indicative of a relationship between the view angle of the X-ray tube and the X-ray output thereof at the X-ray CT scan.

3. The X-ray CT apparatus according to claim 2, wherein the second control device is configured to set the first view angle and the second view angle such that at least one of a position of gravity of the region and a center position of the region with respect to the direction of the view angle coincides with the reference view angle.

4. The X-ray CT apparatus according to claim 3, wherein the graph indicates a distribution of a tube current of the X-ray tube at the time that a tube voltage of the X-ray tube is held constant.

5. An X-ray CT apparatus comprising:
an X-ray tube configured to apply an X-ray onto a subject;
a scan device configured to rotate the X-ray tube about the subject to perform an X-ray CT scan;
a first control device configured to switch an X-ray output of the X-ray tube from a first level to a second level smaller than the first level during the X-ray CT scan when the X-ray tube is placed at a first view angle, and configured to switch the X-ray output of the X-ray tube from the second level to the first level when the X-ray tube is placed at a second view angle different from the first view angle; and
a second control device configured to set the first view angle to be a view angle located short of a third view angle by a first angular width when two angles laterally symmetrical with respect to a reference view angle of the X-ray tube corresponding to the direction of the front of the subject are respectively set to the third view angle and a fourth view angle from the front side of the direction of rotation of the X-ray tube, and configured to set the second view angle to be a view angle located short of the fourth view angle by a second angular width smaller than the first angular width.

6. The X-ray CT apparatus according to claim 1, wherein the reference view angle is a view angle taken when the X-ray tube is located directly above the subject.

7. The X-ray CT apparatus according to claim 1, further comprising an adjusting device configured to adjust the reference view angle according to an operation of an operator.

8. The X-ray CT apparatus according to claim 1, further comprising:
a detecting device configured to detect a posture of the subject, and
an adjusting device configured to adjust the reference view angle, based on the detected posture.

9. The X-ray CT apparatus according to claim 8, further comprising an acquiring device configured to acquire an image taken when the subject is seen in an axial direction,
wherein the detecting device is configured to detect a twist angle at which the direction of a body axis of the subject is taken as a central axis, based on the acquired image, and
wherein the adjusting device is configured to adjust the reference view angle according to the detected twist angle.

10. The X-ray CT apparatus according to claim 8, further comprising an acquiring device configured to acquire an image taken when the subject is seen in an axial direction,
wherein the detecting device is configured to detect lateral positions of the subject, based on the acquired image, and
wherein the adjusting device is configured to adjust the reference view angle according to the detected lateral positions.

11. The X-ray CT apparatus according to claim 8, further comprising an acquiring device configured to acquire an image taken when the subject is seen in an AP direction,
wherein the detecting device is configured to detect lateral positions of the subject, based on the acquired image, and
wherein the adjusting device is configured to adjust the reference view angle according to the detected lateral positions.

12. The X-ray CT apparatus according to claim 11, wherein the image taken is one of an AP scout image, a PA scout image and a coronal tomographic image.

13. The X-ray CT apparatus according to claim 9,
wherein the image taken is an image obtained by a scan of an Nth rotation of the X-ray tube in a helical scan, and
wherein the adjusting device is configured to adjust the reference view angle at a scan of an N+1th rotation of the X-ray tube in the helical scan.

14. The X-ray CT apparatus according to claim 9,
wherein the image taken is an image obtained by an axial scan at a first scan position, and
wherein the adjusting device is configured to adjust the reference view angle at an axial scan at a second scan position close to the first scan position.

15. The X-ray CT apparatus according to claim 1, further comprising a setting device configured to set a rotational speed of the X-ray tube during the X-ray CT scan,
wherein the second control device is configured to set the first view angle and the second view angle as relative view angles from the reference view angle according to the set rotational speed of the X-ray tube.

16. The X-ray CT apparatus according to claim 15, further comprising a selecting device configured to select an imaging region of the subject,
wherein the second control device is configured to set the first view angle and the second view angle according to the selected imaging region.

17. The X-ray CT apparatus according to claim 16, further comprising a storing device configured to store therein candidates for the first view angle and the second view angle according to a combination of the rotational speed and the imaging region,
wherein the second control device determines the candidates each associated with the combination of the set rotational speed and the selected imaging region as the first view angle and the second view angle.

18. The X-ray CT apparatus according to claim 1, wherein the X-ray output of the second level is an X-ray output obtained by multiplying the X-ray output of the first level by a prescribed coefficient smaller than 1.

19. The X-ray CT apparatus according to claim 1, wherein the X-ray output of the first level is an X-ray output which is determined by automatic exposure control and changes according to the view angle of the X-ray tube.

20. A method of performing an X-ray CT scan, comprising:
applying an X-ray to a subject from an X-ray tube;
switching an X-ray output of the X-ray tube from a first level to a second level smaller than the first level when the X-ray tube is placed at a first view angle; and
switching the X-ray output of the X-ray tube from the second level to the first level when the X-ray tube is placed at a second view angle different from the first view angle, wherein the first view angle and the second view angle are set such that an X-ray exposure dose reduced by setting the X-ray output of the X-ray tube smaller than the first level becomes even on right and left sides with respect to a reference view angle of the X-ray tube corresponding to a direction of a front of the subject.

* * * * *